United States Patent [19]

Goble

[11] 4,142,042

[45] Feb. 27, 1979

[54] ALKENYL ETHERS FROM HIGH MOLECULAR WEIGHT POLYOLS

[75] Inventor: Paul H. Goble, Painesville, Ohio

[73] Assignee: Diamond Shamrock Corporation, Cleveland, Ohio

[21] Appl. No.: 839,940

[22] Filed: Oct. 6, 1977

Related U.S. Application Data

[63] Continuation-in-part of Ser. No. 699,178, Jun. 23, 1976, abandoned.

[51] Int. Cl.$^2$ .............................................. C07C 41/10
[52] U.S. Cl. .................................... 536/120; 568/616; 568/673; 568/675
[58] Field of Search ................... 536/120; 260/615 R, 260/615 B

[56] References Cited

U.S. PATENT DOCUMENTS

| | | | |
|---|---|---|---|
| 2,271,873 | 2/1942 | Perkins et al. ................ | 260/615 R |
| 2,924,621 | 2/1960 | Krey et al. ................... | 260/615 R X |
| 3,428,693 | 2/1969 | Prosser ......................... | 260/615 R |
| 3,431,308 | 3/1969 | Zimmerman et al. .......... | 260/615 A |
| 3,445,525 | 5/1969 | Bormann et al. .............. | 260/615 B |
| 3,959,391 | 5/1971 | Allain ........................... | 260/615 B |
| 4,045,472 | 8/1977 | Guthrie ........................ | 260/615 R X |

FOREIGN PATENT DOCUMENTS 226594 1/1969 U.S.S.R. .............................. 260/615 R

OTHER PUBLICATIONS

Nichols et al., J. Amer. Chem. Soc., 67 (1945) 46–49.

*Primary Examiner*—Howard T. Mars
*Attorney, Agent, or Firm*—Bruce M. Winchell

[57] ABSTRACT

Disclosed is a process for preparing alkenyl ethers from high molecular weight polyols in a liquid phase system containing concentrated alkali metal hydroxide, water, water immiscible hydrocarbon solvent and high molecular weight polyol such that the addition of an alkenyl halide results in a reaction which yields an alkenyl ether product which is not readily distillable from the reaction solution at slightly elevated temperatures and atmospheric pressures.

18 Claims, No Drawings

ALKENYL ETHERS FROM HIGH MOLECULAR WEIGHT POLYOLS

CROSS-REFERENCE TO RELATED APPLICATION

This is a continuation-in-part of U.S. Ser. No. 699,178, filed June 23, 1976, now abandoned.

BACKGROUND OF THE INVENTION

The present invention relates generally to a process for reacting high molecular weight polyols with alkenyl halides to produce alkenyl ethers according to the Williamson synthesis. More particularly the present invention relates to a method for forming allyl ethers from high molecular weight polyols reacted with allyl chloride to produce allyl ethers in the presence of flaked sodium hydroxide and entraining solvent such as toluene to produce high yields of the allyl ether. Reaction conditions include: generally atmospheric pressure, a liquid system utilizing a concentrated alkali metal hydroxide, a water immiscible hydrocarbon solvent such as toluene and a high molecular weight polyol in which the hydroxyl groups are the sole functional groups and the alcohol is free from aliphatic unsaturation. Product recovery involves a two phase liquid system for washing the product and later a stripping of the water immiscible solvent since the product is not readily distillable from the reaction solution. Such a method permits the production of allyl ethers without the use of costly components such as dimethylsulfoxide and high pressures associated with processes of past practice.

The Williamson synthesis reaction discovered in 1850 is still the best general method for the preparation of unsymmetrical ethers or for that matter symmetrical ones. The production of an alkenyl ether by this process involves the reaction of a sodium alkoxide with an alkenyl halide such as allyl chloride which evidentally involves an attack of the alkoxide ion upon the polarized carbon-halogen bond in the alkenyl halide by a nucleophic substitution mechanism of the second order. Many of the more complex alkenyl ethers can be prepared in this fashion from polyols with alkenyl halides but the substantial commercial exploration of such a method has been militated against by the cost of some of the materials and ultimately the resultant product. Another problem has been that the reaction conditions have been rather extreme in some cases such as: requiring high pressures, the fact that many of the higher molecular weight materials and the ethers thereby produced are not readily distillable from the reaction mixture. This second problem makes the recovery of a pure product difficult.

Some lower molecular weight materials have been produced from polyols by using an allyl bromide in an excess of 50 percent aqueous sodium hydroxide solution at elevated temperatures. These ethers result when polyols containing free hydroxyl groups are reacted with a hydrocarbon halide, with a halogen preferably bound directly to an aliphatic carbon atom, in the presence of an amount of alkali metal hydroxide at least equivalent to the amount of hydrocarbon halide used. Dimethylsulfoxide is used as a solvent at a temperature up to the boiling point of the dimethylsulfoxide.

The use of allyl chloride has been proposed for substitution in such reactions to yield allyl ethers, but the problem here is that the pressures used in this type of reaction are rather substantial in addition to achieving a rather low yield of product. Furthermore, large excesses of material are used to achieve even moderate yields. Allyl chloride would be preferable to the bromides because of costs.

Thus, it would be extremely advantageous to be able to produce higher molecular weight alkenyl ethers utilizing alkenyl chlorides as a reactant to accomplish good yields under such reaction conditions as to make the process a commercially viable production reaction. Furthermore, it would be advantageous to be able to recover alkenyl ethers which are not readily distillable from the reaction mixture.

SUMMARY OF THE INVENTION

It is therefore an object of the present invention to provide a process toward the preparation of higher molecular weight alkenyl ethers utilizing alkenyl chlorides under such reaction conditions as to produce high yields of alkenyl ethers in a commercially reasonable fashion.

It is another object of the present invention to provide a process for the preparation of higher molecular weight alkenyl ethers which are not readily distillable, in a two phase system such that recovery of a good purity product may be achieved.

These and other objects of the present invention together with the advantages thereof over existing and prior art forms which will become apparent to those skilled in the art from the detailed disclosure of the present invention as set forth hereinbelow, are accomplished by the improvements herein described and claimed.

A process has been found for preparing alkenyl ethers from polyols having more than 15 carbon atoms and a molecular weight less that 6,000 wherein the resultant alkenyl ethers are not readily distillable from the reaction mixture and the process facilitates alkenyl ether product recovery comprising the steps of: establishing a substantially uniform mixture, by stirring at elevated temperatures, consisting essentially of concentrated alkali metal hydroxide, water, water immiscible hydrocarbon solvent and a polyol having more than 15 carbon atoms and a molecular weight less than 6,000 in which 3 to 6 and 10 hydroxyl groups are the sole functional groups and is free from aliphatic unsaturation; azeotropically distilling water and water immiscible hydrocarbon solvent from the system and returning the water immiscible hydrocarbon solvent to the reaction mixture to result in a uniform suspension of finely divided solids in a viscous phase; adding an alkenyl halide to react within the system to yield alkenyl ether product, with the alkenyl halide addition being controlled substantially commensurate with the removal of the water of reaction in the azeotrope, and wherein the alkenyl halide has the halogen atom bound directly to a saturated aliphatic carbon atom; washing the alkenyl ether with water and extracting the aqueous phase to leave an organic phase with the alkenyl ether and the water immiscible hydrocarbon solvent therein; and stripping the water immiscible hydrocarbon solvent from the organic phase to obtain the alkenyl ether.

DESCRIPTION OF THE PREFERRED EMBODIMENT

The process of the present invention is one in which alkenyl ethers may be produced from higher molecular weight polyols without the use of expensive materials used in the past such as alkenyl bromides and dimethylsulfoxide. Additionally, the method of the present invention uses atmospheric pressure thus eliminating much capital expense incurred in the construction of pressure vessels for prior processes. Since flake alkali metal hydroxide may be used in this process the sometimes hazardous use of metallic sodium is thus also eliminated. With nearly stoichiometric amounts of materials yields of alkenyl ethers ranging in the 85 to 99 percent range are achieved, thus this process becomes commercially feasible on a large scale for the production of alkenyl ethers utilizing the Williamson synthesis type chemistry for the process.

The process of the present invention is suitable for use with high molecular weight polyols having more than 15 carbon atoms and a molecular weight of less than 6,000. These polyols should be free from unsaturation and have three to six hydroxyl groups as the sole functional groups. Polyols particularly suited for use in the process of the present invention are: oxypropylated glycerol, oxypropylated trimethylolpropane, oxypropylated trimethylolethane, oxypropylated pentraerythritol, oxypropylated sorbital, oxypropylated mannitol, oxypropylated sucrose, oxypropylated 1,2,5 hexantriol and oxypropylated 1,2,6 hexantriol. Further examples of suitable starting polyols would include the oxyethylated glycerol, oxyethylated trimethylopropane, oxyethylated trimethylolethane, oxyethylated pentraerythritol, oxyethylated sorbitol, oxyethylated mannitol, oxyethylated sucrose, oxyethylated 1,2,5 hexantriol, oxyethylated 1,2,6 hexantriol, oxybutylated glycerol, oxybutylated trimethylolpropane, oxybutylated trimthylolethane, oxybutylated pentraerythritol, oxybutylated sorbitol, oxybutylated mannitol, oxybutylated sucrose, oxybutylated 1,2,5 hexantriol and oxybutylated 1,2,6 hexantriol.

The process utilizes a liquid system wherein alkali metal hydroxide, water immiscible hydrocarbon solvent, water and a polyol are introduced into a reactor and stirred under a relatively inert atmosphere such as nitrogen at a reflux temperature. The amount of water must be sufficient to dissolve the alkali metal hydroxide so that at elevated temperatures with stirring, a substantially uniform mixture results. This permits the use of flaked alkali metal hydroxide material as long as it will completely dissolve in the water present. The water is then removed from the reaction mixture by azeotropically distilling the water and the water immiscible hydrocarbon solvent from the system to result in a uniform suspension of finely divided solids in the viscous phase remaining. As the water is removed, the alkali metal hydroxide slowly precipitates or comes out of solution in the form of finely divided particles such that with stirring of the remaining viscous phase the uniform suspension of the finely divided particles of alkali metal hydroxide occurs. To keep the viscous phase from becoming too viscous to work with, the cooled distillate may be easily separated and the water immiscible hydrocarbon solvent returned to the reaction mixture. When the water removal becomes nearly complete, the nitrogen flow is stopped to the reactor and the alkenyl halide is added in a dropwise fashion to the viscous mixture. The rate of this addition is adjusted to avoid flooding the condensation system attached to the reactor and to prevent a decrease in reaction temperature. Another way of saying this would be to say that the alkenyl halide addition is controlled substantially commensurate with the removal of the water of reaction in the azeotrope. Subsequent to the addition of all of the alkenyl halide so as to provide a stoichiometric amount of alkenyl halide for the theoretical reaction quantities, heating is continued until the water of reaction is removed. When the water removal becomes very slow in a typical operation, the reaction mixture is then cooled to room temperature after which the reactor is filled with distilled water to provide a two phase liquid system. This mixture is stirred vigorously and the phases are then allowed to separate with the aqueous phase being siphoned off and discarded. The remaining liquid phase is then washed with additional washes of distilled water and neutralized with dilute acid such as sulfuric acid to a pH of approximately seven while being stirred rapidly. After each wash with distilled water, the aqueous phase is separated and discarded to leave the organic phase in the reactor vessel. The first wash will remove a major portion of the remaining alkali metal hydroxide and is not neutralized simply because it would require so much acid as to unduly build up the total salts content of this aqueous phase. Because it is also desirable to remove any other unreacted materials which may not be very soluable in a basic solution the subsequent washes are neutralized to improve the solubilities and thus remove more of them by this aqueous extraction process. Any dilute acid will be satisfactory with inorganic acids such as sulfuric acid being preferred. The water immiscible hydrocarbon solvent is then removed by stripping at elevated temperatures under a vacuum in the range of atmospheric to 0.001 millimeters of mercury to result usually in a nonviscous slightly hazy oil which can be cleared by filtering through an appropriate media such as diatomaceous earth.

In the process of the present invention flaked alkali metal hydroxide may be used because of the initial water content of the reaction mixture which upon stirring at elevated temperatures produces a substantially uniform mixture from which the water may thereafter be azeotropically distilled from the reaction mixture with the water immiscible hydrocarbon solvent. Sodium or potassium hydroxide are preferred. Since the polyols above described have more than 15 carbon atoms which result in alkenyl ethers that are not readily distillable, the process of the present invention allows a simple liquid phase separation and finally, a filtering to produce pure product after stripping the water immiscible hydrocarbon solvent. Also the use of a water immiscible hydrocarbon solvent for entraining the solids permits a reaction achieving very high yields in the range of 85 to 99 percent with little attention to recovery of an expensive solvent such as dimethylsulfoxide.

It is felt that the entraining solvent may be any water immiscible hydrocarbon as long as the material forms an azeotrope with water and has a boiling point in the range of 70 to 150 degrees centigrade. This would include aromatic substances such as toluene, xylene and other low molecular weight aromatics in addition to some substituted aliphatic compounds and hydrocarbons like heptane. Naturally this entraining solvent should not be one which would enter into a reaction with the other materials present in the reactor. Based on chemical inertness in this reaction, cost, boiling point and availability, toluene is the preferred solvent.

It is felt that any alkenyl halide may be used in the process of the present invention but because of cost and availability the chlorides are the most desirable. Of the alkenyl chlorides useful in the present invention allyl chloride or 3-chloropropene is the most preferred reactant. It will be noted that use of chlorides can significantly reduce the costs in the present invention since no off-setting capital costs of pressure vessels are incurred in the process of the present invention, because the process of the present invention may be carried out at nearly atmospheric pressures even with the chlorides.

To evaluate the alkenyl ether product, the allyl functionality may be calclulated from a hydroxyl number which is determined analytically. Hydroxyl number determinations are well known and used in the art but basically the alkenyl ether in this case is reacted with a known quantity of acetic anhydride to change the hydroxyl groups to acetate groups thus freeing acetic acid in an amount exactly equal thereto. Titrating the acetic acid will yield the hydroxyl number after calculation. The hydroxyl number may then be inserted into the equation:

$$n = \frac{56{,}100F - M \text{ (OHNo.)}}{56{,}100 + 40 \text{ (OHNo.)}}$$

wherein M equals the molecular weight of the starting polyol, F equals the functionality of the starting polyol to arrive at n which equals the allyl functionality of the resultant alkenyl ether product. This functionality number is an indication of the average level of unsaturation per molecule and shows that the reaction has indeed occurred.

In order that those skilled in the art may more readily understand the present invention and certain preferred aspects by which it may be practiced, the following specific examples are afforded without any intent to limit the scope of the present invention, which is measured by the appended claims.

EXAMPLE 1

An initial charge of 800 g. (8.0 equivalents) of polypropoxylated pentaerythritol having an average molecular weight of 405,320 g. of flaked sodium hydroxide (8.0 equivaltents), 800 g. of toluene and 80 g. of water are introduced into a 5 liter four neck, creased flask which is provided with a stirrer, a thermometer, a pressure equalizing addition funnel topped with a nitrogen inlet, and a Barrett type water trap topped with a Graham condenser. The Barret trap is the same as a Dean and Stark trap with a stopcock at the bottom thereof. This mixture is heated to reflux temperature (106–110° C.) while stirring vigorously and maintaining a slow flow of nitrogen. Refluxing is continued until 76 g. of water are removed. The nitrogen flow is then stopped and 612 g. 3-chloropropene, commonly referred to as allyl chloride (8.0 equivalents), are added dropwise to the viscous mixture. The rate of addition is adjusted to avoid flooding the condenser or a decrease in the reaction temperature. After all of the allyl chloride is added, heating is continued about 1½ hours until most of the water of reaction has removed as evidenced by very slow removal near the end. The reaction mixture is then cooled to room temperature after which the flask is filled with distilled water. The mixture is stirred vigorously for five minutes, the phases are allowed to separate, and the aqueous phase is siphoned off and discarded. About 1400 ml. of water are then added to the flask and the mixture is neutralized (pH 7) with 4½ ml. of 6N $H_2SO_4$ while being stirred rapidly. The phases are allowed to separate and the aqueous phase is discarded. The organic phase is washed a third and a fourth time with 1400 ml. and 1000 ml. distilled water, respectively, with the aqueous phase being separated and discarded each time. Thereafter, about 650 g. of toluene are then removed by stripping at 95° C. under a vacuum of about 0.1 mm. of mercury giving 1004 g. of a nonviscous, slightly hazy oil. A clear product is obtained by filtering through diatomaceous earth.

The hydroxyl number equaled 55 (mg. KOH/g). The calculated allyl functionality was 3.47. The yield was 93% of theory, calculated on the polyol and 81% of theory, calculated on allyl chloride.

EXAMPLE 2

An initial charge of 800 g. of polypropoxylated pentaerythritol (8.0 equivalents), 320 g. of flaked sodium hydroxide (8.0 equivalents), 800 g. of toluene and 80 g. of water are introduced into the reaction flask described in Example 1. The mixture is reacted as described in Example 1 except that the addition of 614 g. of 3-chloropropene, commonly referred to as allyl chloride (8.0 equivalents), is started after 63.5 g. of water have been azeotroped. After all of the allyl chloride has been added, heating is continued 1½ hours until the azeotroping of water becomes very slow. The reaction mixture is then cooled to room temperature, two liters of distilled water are added, the mixture is stirred five minutes, the phases are allowed to separate, and the aqueous phase is siphoned off and discarded. One liter of water is then added to the flask after which the mixture is stirred rapidly and neutralized to pH 7 with about four ml. of 6N $H_2SO_4$. The phases are allowed to separate and the aqueous phase is discarded. The organic phase is washed a third time with one liter of distilled water. After the aqueous phase is discarded, the organic phase is stripped at 95° C. under a vacuum of about 25 mm. of mercury and then finally at 0.09 mm. of mercury. The slightly hazy resin is filtered through diatomaceous earth while hot, resulting in 1045 g. of a clear, low viscosity, yellow product.

The hydroxyl number equaled 50 (mg. KOH/g.). The calculated allyl functionality was 3.52. The yeild was 97 percent of theory, calculated on the polyol and 85 percent of theory calculated on the allyl chloride.

EXAMPLE 3

An initial charge of 229 g. (2.0 equivalents) of polypropoxylated sorbitol having an average molecular weight of 760, 80 g. of flaked sodium hydroxide (2.0 equivalents) and 200 g. of toluene are placed into a 1 liter flask which is provided with a stirrer, a thermometer, a pressure equalizing addition funnel topped with a nitrogen inlet, and a Barrett-type water trap topped with a condenser. This mixture is heated to about 91° C. and 20 ml. of distilled water are added. The mixture is then heated to reflux temperature under the conditions specified in Example 1. After 18 g. of water are removed azeotropically, 158 g. of 3-chloropropene, commonly referred to as allyl chloride, (2.07 equivalents) are added as described in Example 1. Heating is continued for 15 minutes after the allyl chloride addition is completed. About 50 g. of water were azeotroped from the mixture during the reaction. The mixture is cooled and 300 ml. of distilled water are added. The mixture is stirred and neutralized with 38 ml. of 6.45N $H_2SO_4$. The aqueous phase is separated and discarded. The organic phase is washed with a second 300 ml. portion of water which is then neutralized with about 1½ ml. of 6.45N $H_2SO_4$. The aqueous wash solution is separated from the organic phase and discarded. The organic phase is placed in a rotary evaporator and then solvent is stripped at 95° C. and 0.3 mm. of mercury, 280 g. of an orange-colored product is obtained. A clear oil is obtained by filtering through diatomaceous earth.

The hydroxyl number equaled 81 (mg. KOH/g.). The caluclated allyl functionality was 4.73. The yield was 96% of theory, calculated on the polyol and 76% of theory, calculated on allyl chloride.

Thus it should be apparent from the foregoing description of the preferred embodiment that the process herein described accomplishes the objects of the invention and solves the problems attendant to the preparation of alkenyl ethers from high molecular weight polyols and alkenyl halides.

What is claimed is:

1. A process for preparing alkenyl ethers from polyols having more than 15 carbon atoms and a molecular weight less than 6,000 wherein the resultant alkenyl ethers are not readily distillable from the reaction mixture and the process facilitates ether product recovery, comprising the steps of: establishing a substantially uniform mixture, by stirring at elevated temperatures, the mixture consisting of alkali metal hydroxide, sufficient water as to dissolve the alkali metal hydroxide, water immiscible hydrocarbon solvent, and a polyol having more than 15 carbon atoms and a molecular weight less than 6,000 in which 3 to 6 or 10 hydroxyl groups are the sole functional groups and is free from aliphatic unsaturation; azeotropically distilling water and water immiscible hydrocarbon solvent from the system and returning the water immiscible hydrocarbon solvent to the reaction mixture to result in a uniform suspension of finely divided solids in a viscous phase; adding an alkenyl chloride, containing a chlorine atom bound directly to a saturated aliphatic carbon atom, after removal of water is near completion, in a dropwise fashion, at a rate to maintain the temperature of reaction; removing most of the water of reaction; cooling the reaction mixture; washing the reaction mixture with water; separating the organic phase; and stripping the water immiscible hyhydrocarbon solvent from the organic phase to obtain the alkenyl ether; wherein the entire process is conducted at atmospheric or subatmospheric pressures.

2. A process according to claim 1 wherein the water immiscible hydrocarbon solvent forms an azeotrope with water and has a boiling point in the range of 70 to 150 degrees centigrade.

3. A process according to claim 2 wherein the water immiscible hydrocarbon solvent is toluene.

4. A process according to claim 1 wherein the alkali metal hydroxide is a flaked material selected from the group of sodium hydroxide or potassium hydroxide.

5. A process according to claim 1 wherein upon allowing the two phases to separate the phases are neutralized to a pH of about seven with an acidic substance.

6. A process according to claim 1 wherein the water immiscible hydrocarbon solvent is stripped from the alkenyl ether product by means of vacuum distillation at a temperature in the range of 50 to 150 degrees centigrade with a vacuum in the range of atmospheric to 0.001 millimeters of mercury.

7. A process according to claim 1 wherein the alkenyl chloride is 3-chloropropene.

8. A process for preparing allyl ethers from polyols having more than 15 carbon atoms and a molecular weight less than 6,000 in high yields comprising the steps of: establishing a substantially uniform mixture, by stirring at elevated temperatures the mixture, consisting of alkali metal hydroxide, sufficient water to dissolve the alkali metal hydroxide, toluene so as to form an azeotrope with the water and a polyol having more than 15 carbon atoms and a molecular weight less than 6,000 in which 3 to 6 or 10 hydroxyl groups are the sole functional groups and is free from aliphatic unsaturation; azeotropically distilling water and toluene from the system at nearly atmospheric pressure, and returning the toluene to the mixture, to result in a uniform suspension of finely divided solids in a viscous phase; adding allyl chloride after removal of water is near completion, in a dropwise fashion, at a rate to maintain the temperature of reaction, removing most of the water of reaction; cooling the reaction mixture; washing the reaction mixture with water; and recovering the allyl ether from the reaction mixture; wherein the entire process is conducted at atmospheric or subatmospheric pressures.

9. A process according to claim 8 wherein the polyol is selected from the group of oxypropylated glycerol, oxypropylated trimethylolpropane, oxypropylated trimethylolethane, oxypropylated pentraerythritol, oxypropylated sorbitol, oxypropylated mannitol, oxypropylated sucrose, oxypropylated 1,2,5 hexantriol and oxypropylated 1,2,6 hexantriol, oxyethylated glycerol, oxyethylated trimethylolpropane, oxyethylated trimethylolethane, oxyethylated pentraerythritol, oxyethylated sorbitol, oxyethylated mannitol, oxyethylated sucrose, oxyethylated 1,2,5 hexantriol, oxyethylated 1,2,6 hexantriol, oxybutylated glycerol, oxybutylated trimethylolpropane, oxybutylated trimethylolethane, oxybutylated pentraerythritol, oxybutylated sorbitol, oxybutylated mannitol, oxybutylated sucrose, oxybutylated 1,2,5 hexantriol and oxybutylated 1,2,6 hexantriol.

10. A process according to claim 8 wherein the polyol is oxypropylated glyerol.

11. A process according to claim 8 wherein the polyol is oxypropylated trimethylolpropane.

12. A process according to claim 8 wherein the polyol is oxypropylated trimethylolethane.

13. A process according to claim 8 wherein the polyol is oxypropylated pentraerythritol.

14. A process according to claim 8 wherein the polyol is oxypropylated sorbitol.

15. A process according to claim 8 wherein the polyol is oxypropylated mannitol.

16. A process according to claim 8 wherein the polyol is oxypropylated sucrose.

17. A process according to claim 8 wherein the polyol is oxypropylated 1,2,5 hexantriol.

18. A process according to claim 8 wherein the polyol is oxypropylated 1,2,6 hexantriol.

* * * * *